United States Patent [19]

Chesterfield et al.

[11] Patent Number: 5,447,100
[45] Date of Patent: Sep. 5, 1995

[54] APPARATUS FOR CALENDERING SUTURES IN ORTHOGONAL DIRECTIONS

[75] Inventors: Michael P. Chesterfield, Norwalk; Mark P. Reale, Trumbull, both of Conn.

[73] Assignee: United States Surgical Corporation, Norwalk, Conn.

[21] Appl. No.: 195,405

[22] Filed: Feb. 14, 1994

Related U.S. Application Data

[60] Division of Ser. No. 27,570, Mar. 5, 1993, Pat. No. 5,312,642, which is a continuation of Ser. No. 652,939, Feb. 8, 1991, abandoned.

[51] Int. Cl.⁶ ................................. B30B 3/04
[52] U.S. Cl. ...................... 100/161; 28/240; 100/171; 100/176
[58] Field of Search .............. 100/42, 158 R, 159, 100/161, 171, 176; 68/22 R; 28/219, 240, 245, 268, 269, 299; 19/0.3, 0.48; 606/228-231

[56] References Cited

U.S. PATENT DOCUMENTS

| | | | |
|---|---|---|---|
| 2,216,142 | 10/1940 | Taylor et al. | 264/282 |
| 2,442,279 | 5/1948 | Alderfer | 28/219 |
| 2,703,423 | 3/1955 | Hunt | 100/171 |
| 2,838,799 | 7/1958 | Meister | 264/129 |
| 2,940,868 | 6/1960 | Patchell | 427/2.31 |
| 2,966,198 | 12/1960 | Loylde | 156/180 |
| 3,192,597 | 7/1965 | McIntosh et al. | 28/240 |
| 3,257,702 | 6/1966 | Kurtz | 28/167 |
| 3,307,971 | 3/1967 | Kurtz | 428/395 |
| 3,317,333 | 5/1967 | Halliday | 427/175 |
| 3,322,125 | 5/1967 | Kurtz | 606/230 |
| 3,379,552 | 4/1968 | Kurtz | 427/175 |
| 3,463,657 | 8/1969 | Schuster | 427/348 |
| 3,527,650 | 9/1970 | Block | 87/1 |
| 3,565,077 | 2/1971 | Glick | 606/231 |

(List continued on next page.)

FOREIGN PATENT DOCUMENTS

| | | |
|---|---|---|
| 0046039 | 2/1982 | European Pat. Off. |
| 0128733 | 12/1984 | European Pat. Off. |
| 0131868 | 1/1985 | European Pat. Off. |
| 0136490 | 4/1985 | European Pat. Off. |
| 0147178 | 7/1985 | European Pat. Off. |
| 0150572 | 8/1985 | European Pat. Off. |
| 0177915 | 4/1986 | European Pat. Off. |
| 0267015 | 5/1988 | European Pat. Off. |
| 2297051 | 1/1976 | France |
| 779291 | 7/1957 | United Kingdom |
| 811369 | 4/1959 | United Kingdom ............ 100/176 |
| 924806 | 5/1963 | United Kingdom ............ 100/171 |
| 2092155 | 8/1982 | United Kingdom |
| 2162851 | 2/1986 | United Kingdom |
| 2172890 | 10/1986 | United Kingdom |
| 83/04030 | 11/1983 | WIPO |
| 85/01284 | 3/1985 | WIPO |
| 85/03698 | 8/1985 | WIPO |
| 86/02271 | 4/1986 | WIPO |

OTHER PUBLICATIONS

Gilding, D. K., et al. *Biodegradable Polymers for Use in Surgery—Polyglycolic/Poly(lactic acid) Homopolymer and Copolymers*, 1 Polymer, vol. 20, pp. 1459-1464 (1979).

Williams, D. F. (ed), *Biocompatability of Clinical Implant Materials*, vol. 11, Ch. 9: "Biodegradable Polymers" (1981).

Lynch et al., *Growth Factors in Wound Healing*, J. Clin. Invest., vol. 84, pp. 640-645 (Aug. 1989).

"Quantitative Evaluation of Stiffness of Commercial Suture Materials", C. C. Chu, Ph.D., Surgery, Gynecology & Obstetrics, Mar. 1990, vol. 168, pp. 233-238.

*Primary Examiner*—Stephen F. Gerrity

[57] ABSTRACT

A method for calendering a suture includes passing the suture lengthwise between two pairs of calendering rollers each pair being oriented orthogonally to the other pair. The suture may be coated and/or filled by passing it through the contacting region of a suture filling applicator to which filling agent is supplied by a metering pump. The filling process may be computer controlled.

4 Claims, 6 Drawing Sheets

U.S. PATENT DOCUMENTS

| | | | |
|---|---|---|---|
| 3,665,927 | 5/1972 | Kurtz | 606/231 |
| 3,700,489 | 10/1972 | Borysko | 427/2.28 |
| 3,754,069 | 8/1973 | Adams et al. | 264/131 |
| 3,839,524 | 10/1974 | Adams et al. | 264/131 |
| 3,867,190 | 2/1975 | Schmitt et al. | 427/2.25 |
| 3,883,497 | 5/1975 | Gregory et al. | 530/300 |
| 3,917,824 | 11/1975 | Camble et al. | 514/12 |
| 3,942,532 | 3/1976 | Hunter et al. | 606/231 |
| 3,948,875 | 4/1976 | Cohen et al. | 530/399 |
| 3,982,543 | 9/1976 | Schmitt et al. | 606/230 |
| 4,020,196 | 4/1977 | Guillermin et al. | 427/255.5 |
| 4,027,676 | 6/1977 | Mattei | 606/230 |
| 4,047,533 | 9/1977 | Perciaccante et al. | 606/230 |
| 4,185,637 | 1/1980 | Mattei | 606/230 |
| 4,201,216 | 5/1980 | Mattei | 606/230 |
| 4,232,067 | 11/1980 | Coleman | 428/17 |
| 4,338,397 | 7/1982 | Gilbert et al. | 435/69.1 |
| 4,418,691 | 12/1983 | Yannas et al. | 424/548 |
| 4,429,080 | 1/1984 | Casey et al. | 525/415 |
| 4,438,253 | 3/1984 | Casey et al. | 528/86 |
| 4,452,973 | 6/1984 | Casey et al. | 528/354 |
| 4,470,941 | 9/1984 | Kurtz | 264/136 |
| 4,528,186 | 7/1985 | Nishimura et al. | 530/324 |
| 4,532,154 | 7/1985 | Hardeman | 427/175 |
| 4,532,929 | 8/1985 | Mattei et al. | 606/230 |
| 4,584,347 | 4/1986 | Harpell et al. | 525/119 |
| 4,589,942 | 5/1986 | Korinek | 156/148 |
| 4,621,052 | 11/1986 | Sugimoto | 435/70.2 |
| 4,705,820 | 11/1987 | Wang et al. | 5224/381 |
| 4,711,241 | 12/1987 | Lehmann | 606/230 |
| 4,716,620 | 12/1987 | Casey et al. | 525/408 |
| 4,717,717 | 1/1988 | Finkenaur | 514/21 |
| 4,743,679 | 5/1988 | Cohen | 530/350 |
| 4,861,757 | 8/1989 | Antoniades et al. | 514/21 |
| 4,872,276 | 10/1989 | Godfrey | 38/101 |
| 4,874,746 | 10/1989 | Antoniades et al. | 514/21 |
| 4,911,927 | 3/1990 | Hill et al. | 424/443 |
| 4,944,948 | 7/1990 | Uster et al. | 424/450 |
| 4,994,303 | 2/1991 | Calkins | 427/173 |
| 5,021,265 | 6/1991 | Balde et al. | 427/365 |
| 5,181,923 | 1/1993 | Chesterfield et al. | 606/228 |

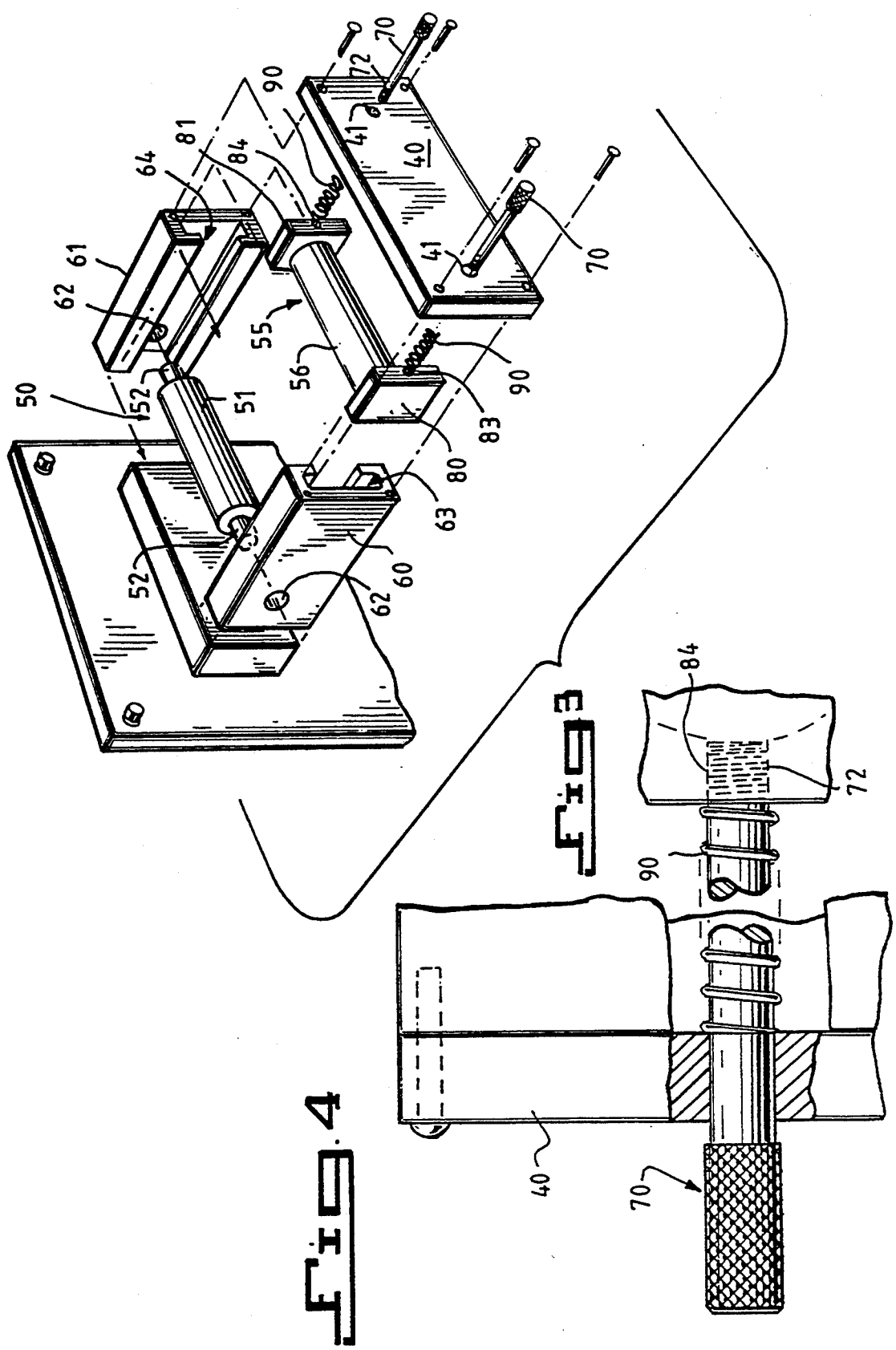

APPARATUS FOR CALENDERING SUTURES IN ORTHOGONAL DIRECTIONS

This is a divisional of U.S. application Ser. No. 08/027,570, filed Mar. 5, 1993, now U.S. Pat. No. 5,312,642, which is a continuation of application Ser. No. 07/652,939, filed Feb. 8, 1991, now abandoned.

BACKGROUND OF THE INVENTION

1. Field of the Invention

This invention pertains to a method and apparatus for mechanically treating sutures, and especially to a method and apparatus for calendering multifilament surgical sutures.

2. Background of the Art

An important consideration in performing surgery is the "hand" or "feel" of the suture being used to close wounds, which is reflected at least in part by the knot tie-down and run-down characteristics of the suture. "Tie-down characteristics" refers to the facility with which a surgeon can tie a knot, and the ability of the suture to remain knotted without spontaneously unravelling. "Run-down characteristics" refers to the ability of a surgeon to make one or more "throws" of a knot in the suture and have it run down a suture to the knot site. Generally, hand or feel of a suture and tie-down characteristics relate to the lubricity and stiffness of the suture: lubricity facilitates the tying of a knot whereas stiffness makes tying a tight knot more difficult and increases the probability of kinking of the suture and/or unravelling of the knot.

Both multifilament sutures and monofilament sutures are known in the art. Multifilament sutures, such as braided or twisted sutures, have better softness and flexibility than monofilament sutures and can be more easily knotted. However, multifilament sutures can have a rougher surface or "grabbiness" than monofilament sutures and a significant percentage of dead space or interstices between the filaments. The dead space can be reduced by impregnating the multifilament suture with a filler material. Filler material can help lubricate the suture fibers and enhance flexibility.

Coatings improve the knot run down characteristics of a suture, although they also tend to increase stiffness. Another source of stiffness arises from the commonly employed process of "heat setting" or "hot stretching" the suture, such as described in U.S. Pat. Nos. 3,322,125, 3,257,702, 3,379,552, and 3,839,524, for example. It has been proposed to improve the flexibility of heat set sutures by flexing the suture as disclosed in U.S. Pat. Nos. 3,839,524, and 3,257,702.

Known materials for filling or coating sutures are described in U.S. Pat. Nos. 3,322,125, 3,379,552, 3,867,190, 3,942,532, 4,047,533, 4,532,929, 4,201,216, and 4,711,241, for example.

However, the uniformity of the filling or coating remains as an important concern in the fabrication of sutures. Non-uniformity can hamper the effectiveness of the filler and coating, and an apparatus and method which addresses this issue is needed.

SUMMARY OF THE INVENTION

An apparatus is provided herein for calendering multifilament sutures. The apparatus comprises a frame; and first and second pairs of rollers. The first pair of rollers includes a first roller and a second roller, which are rotatably mounted to the frame, the first and second rollers being substantially parallel to each other. At least one of the first and second rollers is resiliently biased towards the other so as to apply a predetermined amount of compressive force to a suture located therebetween. The second pair of rollers includes a third roller and a fourth roller, which are also rotatably mounted to the frame. The third and fourth rollers are substantially parallel to each other and substantially orthogonal to the first pair of rollers. At least one of the third and fourth rollers is resiliently biased towards the other so as to apply a predetermined amount of compressive force to a suture located therebetween.

Each of the rollers is substantially cylindrical and has a polished suturecontacting surface with a surface smoothness of from about 4 microinches to about 16 microinches.

BRIEF DESCRIPTION OF THE DRAWINGS

FIG. 3 is an exploded perspective view of the upper calendering portion;

FIG. 4 is a partially cutaway sectional view of the spring mounting of the calender apparatus;

DETAILED DESCRIPTION OF PREFERRED EMBODIMENTS

Figure 1:
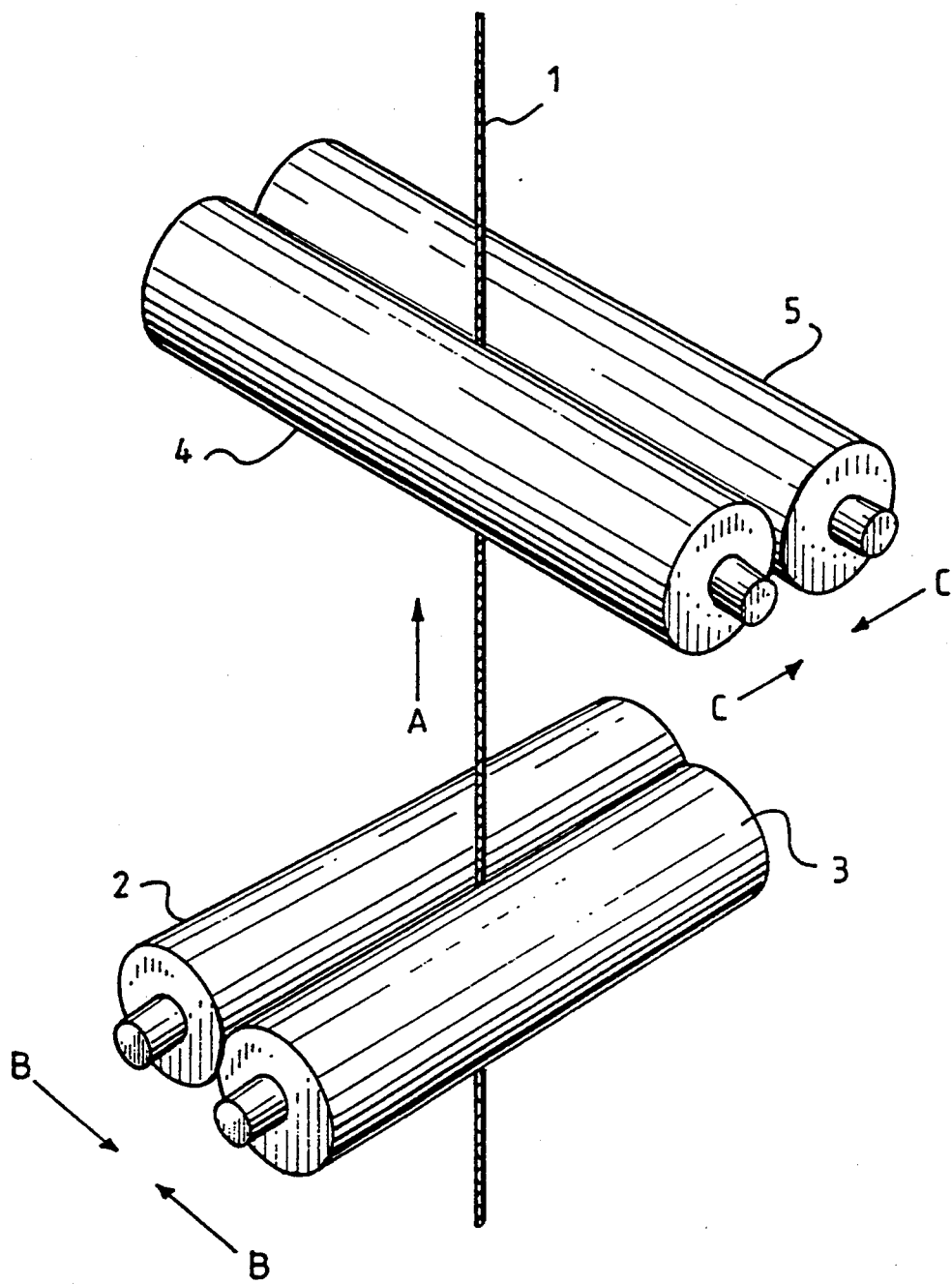
FIG. 1 is a diagrammatic illustration of the calendering apparatus of the present invention.

The present invention is primarily directed to the treatment of braided surgical sutures to facilitate and promote substantially uniform and complete coating and/or filling of the suture. In the preferred embodiment braided synthetic absorbable sutures are calendered prior to filling with a storage stabilizing agent, preferably a mixture containing glycerol, in order to promote substantially complete penetration of the filler throughout the braid structure.

However, the calendering method and apparatus may also find application to coating and/or filling of absorbable or non-absorbable sutures. To facilitate understanding the invention, possible suture materials and braid constructions, coatings and fillers, possibly containing one or more therapeutic agents or growth factors, will be discussed prior to describing in detail the preferred calendering apparatus and method and the preferred method for calendering braided synthetic absorbable sutures prior to filling with a stabilizing agent.

Suture Material and Construction

As stated, the calendering method and apparatus finds particular application to the treatment of braided multifilament surgical sutures. The term "braid" means a substantially symmetrical strand formed by crossing a number (at least three) of individual strands composed of one or more filaments diagonally in such manner that each strand passes alternatively over and under one or more of the others. The braid may include a core section composed of one or more filaments around which the braid is externally fabricated, although such core may be excluded, if desired. The braid may be of traditional construction (so-called "hollow" or "tubular"

braid) or may be of spiroid construction, with or without a core. Preferred braid constructions of the traditional type are disclosed and claimed in U. S. Pat. No. 5,019,093 and related cases, hereby incorporated by reference.

The braided suture can be fabricated from a wide variety of natural and synthetic fibrous materials such as any of those heretofore disclosed for the construction of sutures. Such materials include non-absorbable as well as partially and fully bio-absorbable (i.e., resorbable) natural and synthetic fiber-forming polymers. Non-absorbable materials which are suitable for fabricating the braided suture of this invention include silk, polyamides, polyesters, polypropylene, silk, cotton, linen, etc. Carbon fibers, steel fibers and other biologically acceptable inorganic fibrous materials can also be employed. Bio-absorbable resins from which the suture can be fabricated include those derived from glycolic acid, glycolide, lactic acid, lactide, dioxanone, epsilon-caprolactone, trimethylene carbonate, etc., and various combinations of these and related monomers. Sutures prepared from resins of this type are known in the art, e.g., as disclosed in U.S. Pat. Nos. 2,668,162; 2,703,316; 2,748,987, 3,225,766; 3,297,033; 3,422,181; 3,531,561; 3,565,077; 3,565,869; 3,620,218; 3,262,948; 3,636,956; 3,736,646; 3,772,420; 3,773,919; 3,792,010; 3,797,499; 3,839,297; 3,867,190; 3,787,284; 3,982,543; 4,047,533; 4,060,089; 4,137,921; 4,157,437; 4,234,775; 4,237,920; 4,300,565; and 4,523,591; U.K. Patent No. 779,291; D. K. Gilding et al., "Biodegradable polymers for use in surgery—polyglycolic/poly(lactic acid) homo-and co-polymers: 1, Polymer, Volume 20, pages 1459-1464 (1979), and D. F. Williams (ed), Biocompatibility of Clinical Implant Materials, Vol. II, Ch. 9: "Biodegradable Polymers (1988).

Filling Agent

When a multifilament suture is fabricated from a material which is susceptible to hydrolysis, e.g., any of the absorbable resins previously mentioned, prior patents teach that extreme care must be taken to rigorously exclude moisture from contacting the suture during storage or to otherwise preserve the suture from excessive hydrolytic attack which would compromise its in vitro strength to the point where the suture would no longer be serviceable.

Thus, according to U.S. Pat. Nos. 3,728,839 and 4,135,622, the in vivo strength of polyglycolic acid surgical elements such as sutures undergoes significant deterioration on long term standing in the package even on exposure of the contents to very small amounts of water for very short periods of time, e.g., 20 minutes or less, just prior to packaging due to the tendency of a moisture impervious package to seal the moisture in with the suture. To prevent or minimize the extent of hydrolytic degradation of an absorbable suture during storage, U.S. Pat. Nos. 3,728,839 and 4,135,622 disclose removing substantially all moisture from the suture before sealing the package. This approach to improving the suture's storage stability, while effective, is in practice difficult and expensive to carry out. Prior to sealing the suture within its moisture impervious package, it is essential that the suture be "bone dry" a condition achieved by heating the suture for a sufficient period to remove essentially all water therefrom, e.g., 180°-188° for 1 hour under a 26 inch vacuum. However, once the water is removed, the suture cannot be allowed to contact a moisture-containing environment even for a limited duration since as previously noted, the patents teach that even brief exposure to moisture can cause severe deterioration of suture in vivo strength. It therefore becomes necessary following the water removal step to temporarily store the suture in a dry area, i.e., an environment which is essentially free of moisture, where the possibility of contact with moisture is largely eliminated. These operations for improving the storage stability of an absorbable suture are time consuming, expensive and constitute a relatively complex solution to the storage stability problem.

In an entirely different approach to improving the storage stability of an absorbable suture, one that avoids the foregoing drawbacks associated with the method of U.S. Pat. Nos. 3,728,839 and 4,135,622, the storage stability of an absorbable braided suture which is susceptible to hydrolysis is improved by applying to the suture a storage stabilizing amount of a filler material containing at least one water soluble liquid polyhydroxy compound and/or ester thereof. In addition to imparting an enhanced degree of storage stability to the suture, practice of this embodiment of the present invention confers other benefits as well. So, for example, a braided suture which has been filled with a storage stabilizing amount of, e.g., glycerol, exhibits better flexibility and "hand" characteristics than the untreated suture. Moreover, since the polyhydroxy compounds are generally capable of dissolving a variety of medico-surgically useful substances, they can be used as vehicles to deliver such substances to a wound or surgical site at the time the suture is introduced into the body.

The useful storage stabilizing agents are generally selected from the water soluble, liquid polyhydroxy compounds and/or esters of such compounds, preferably those having no appreciable toxicity for the body at the levels present. The expression "liquid polyhydroxy compound" contemplates those polyhydroxy compounds which in the essentially pure state are liquids, as opposed to solids, at or about ambient temperature, e.g., at from about 15° C. to about 40° C. The preferred polyhydroxy compounds possess up to about 12 carbon atoms and where the esters are concerned, are preferably the monoesters and diesters. Among the specific storage stabilizing agents which can be used with generally good results are glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolproprane, pentaerythritol, sorbitol, and the like. Glycerol is especially preferred. Mixtures of storage stabilizing agents, e.g., sorbitol dissolved in glycerol, glycerol combined with monoacetin and/or diacetin, etc., are also useful.

To prevent or minimize run-off or separation of the storage stabilizing agent from the suture, a tendency to which relatively low viscosity compounds such as glycerol are especially prone, it can be advantageous to combine the agent with a thickener. Many kinds of pharmaceutically acceptable non-aqueous thickeners can be utilized including water-soluble polysaccharides, e.g., hydroxypropyl methylcellulose (HPMC), and the other materials of this type which are disclosed in European Patent Application 0 267 015, polysaccharide gums such as guar, xanthan, and the like, gelatin, collagen, etc. An especially preferred class of thickeners are the saturated aliphatic hydroxycarboxylic acids of up to about 6 carbon atoms and the alkali metal and alkaline earth metal salts and hydrates thereof. Within this preferred class of compounds are those corresponding to the general formula

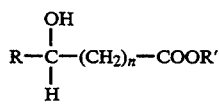

wherein R is hydrogen or methyl, R' is a metal selected from the group consisting of alkali metal and alkaline earth metal and n is 0 or 1, and hydrates thereof. Specific examples of such compounds include salts of lactic acid such as calcium lactate and potassium lactate, sodium lactate, salts of glycolic acid such as calcium glycolate, potassium glycolate and sodium glycolate, salts of 3-hydroxy propanoic acid such as the calcium, potassium and sodium salts thereof, salts of 3-hydroxybutanoic acid such as calcium, potassium and sodium salts thereof, and the like. As stated hereinabove, hydrates of these compounds can also be used. Calcium lactate, especially calcium lactate pentahydrate, is a particularly preferred thickener.

Where a thickener is utilized, it will be incorporated in the filling composition in at least that amount required to increase the overall viscosity of the storage stabilizing agent to the point where the agent no longer readily drains away from the suture in a relatively short period. In the case of a preferred storage stabilizing agent-thickener combination, namely, glycerol and calcium lactate, the weight ratio of glycerol to calcium lactate can vary from about 1:1 to about 10:1 and preferably is from about 6:1 to 8:1.

If necessary or desirable, the storage stabilizing agent together with optional thickener can be dissolved in any suitable non-aqueous solvent or combination of solvents prior to use. To be suitable, the solvent must (1) be miscible with the storage stabilizing agent and optional thickener, if present (2) have a sufficiently high vapor pressure to be readily removed by evaporation, (3) not appreciably affect the integrity of the suture and (4) be capable of wetting the surface of the suture. Applying these criteria to a preferred storage stabilizing agent, glycerol, advantageously in admixture with a preferred thickener, calcium lactate, lower alcohols such as methanol and ethanol are entirely suitable solvent carriers. When a solvent is utilized in the preparation of the stabilizing agent, e.g., methanol, such solvent can be employed in amounts providing a solution concentration of from about 20% to about 50%, preferably about 30% to about 45%, by weight of the storage stabilizing agent including any optional thickener.

Preparing the storage stabilizing agent for application to the suture is a relatively simple procedure. For example, in the case of a mixture of glycerol and calcium lactate, the desired amount of glycerol is first introduced to a suitable vessel followed by the addition thereto of the desired amount of calcium lactate. If no solvent is to be used, the mixture is then thoroughly mixed. Where a solvent such as methanol is employed, the solvent is added to the mixture of glycerol and calcium lactate and the solution is then thoroughly mixed to dissolve the compounds.

Application of the storage stabilizing agent to the suture can be carried out in any number of ways. Thus, for example, the suture can be submerged in the storage stabilizing agent or solution thereof until at least a storage stabilizing amount of agent is acquired or otherwise retained by the suture, even after the optional removal of any excess agent and/or accompanying solvent (if present) such as by drainage, wiping, evaporation, etc. In many cases, contact times on the order of from just a few seconds, e.g., about 10 seconds or so, to several hours, e.g., about 2 hours and even longer, are sufficient to impart a substantial improvement in the storage stability of the treated suture compared to the same suture which has not been treated with storage stabilizing agent.

The foregoing method of contacting the suture with the storage stabilizing agent can be conducted continuously or in batch. Thus, a running length of the suture can be continuously passed through a quantity of stabilizing agent at a velocity which has been previously determined to provide the necessary degree of exposure, or contact time, of the suture with the storage stabilizing agent. As the suture emerges from the storage stabilizing agent, it can be passed through a wiper or similar device to remove excess agent prior to the packaging operation. Preferably, the suture is passed through a coating head supplied by a metering pump with a constant supply of filling solution, with the suture emerging from the coating head and passing through an evaporation oven to remove the filling solution solvent prior to any further surface contact, i.e., with rollers, etc. In a batch operation, a quantity of suture is merely submerged within the storage stabilizing agent for the requisite period of time with any excess agent being removed from the suture if desired.

Alternatively, the storage stabilizing agent and solutions thereof can be applied to the suture by spraying, brushing, wiping, etc. such that the suture receives and retains at least a storage stabilizing amount of the agent.

Yet another procedure which can be used to apply the storage stabilizing agent involves inserting suture in a package containing an effective amount of the agent such that intimate contact between the suture and the agent is achieved.

Whatever the contacting procedure employed, it is necessary that the suture being treated acquire a storage stabilizing amount of the storage stabilizing agent. In general, amounts from about 2 to about 25, and preferably from about 5 to about 15, weight percent of storage stabilizing agent(s) (exclusive of any solvent) by weight of the suture contacted therewith is sufficient to provide significantly improved storage stability compared to that of the untreated suture.

As previously pointed out, a filled braided suture component in accordance with the invention need not be packaged and maintained under the very dry conditions required for prior synthetic absorbable sutures. Instead, it is preferred that the filled sutures be equilibrated so that the level of moisture or other stabilizing agent solvent is sufficient to result in an appropriate viscosity level for the stabilizing agent and thickener in order to keep the stabilizing agent on the suture. In the preferred embodiment of a braided suture filled with a mixture of glycerol and calcium lactate, the moisture level may be equilibrated to as low as about 0.2% by weight of the suture, and is preferably above 0.3% or, even more preferably, above 0.5% by weight of the suture.

Indeed, it has been found that a braided suture filled with a glycerol/calcium lactate composition tends to undergo undesirable changes if exposed to a very dry environment. More particularly, if such a filled suture is exposed to a very dry environment, the surface of the suture may accumulate a flaked or powdered substance which could possibly interfere with, or render more difficult, the removal of the suture from its package. Exposure of sutures filled with a glycerol stabilizing agent to vacuum has been found to adversely decrease the level of glycerol filler, possibly by vaporizing the glycerol. Equilibrating the filled suture, such as in a dew point controlled environment, so that the suture contains a relatively high moisture level, e.g., in excess of 0.2% and preferably in excess of 0.5% by weight of the suture, prevents such accumulation of flaked or powdered substances which might otherwise result were the suture exposed to an extremely dry environment. Conversely, the presence of too much moisture can also have deleterious effects, such as causing the glycerol filling to run. Therefore, it is preferable to control the moisture level within a range having preset upper and lower limits.

Therapeutic Agents and/or Growth Factors

It is also within the scope of the invention to impregnate the braided suture of this invention with, or otherwise apply thereto, one or more medico-surgically useful substances, e.g., those which accelerate or beneficially modify the healing process when the suture is applied to a wound or surgical site. So, for example, the braided suture herein can be provided with a therapeutic agent which will be deposited at the sutured site. The therapeutic agent can be chosen for its antimicrobial properties, capability for promoting wound repair and/or tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a surgical or trauma wound site.

To promote wound repair and/or tissue growth, one or more biologically active materials known to achieve either or both of these objectives can be applied to the braided suture. Such materials include any of several Human Growth Factors (HGFs), magainin, tissue or kidney plasminogen activator to cause thrombosis, superoxide dismutase to scavenge tissue damaging free radicals, tumor necrosis factor for cancer therapy, colony stimulating factor, interferon, interleukin-2 or other lymphokine to enhance the immune system, and so forth.

The term "Human Growth Factor" or "HGF" embraces those materials, known in the literature, which are referred to as such and include their biologically active loosely related derivatives. The HGFs can be derived from naturally occurring sources including human and non-human sources, e.g., bovine sources, and are preferably produced by recombinant DNA techniques. Specifically, any of the HGFs which are mitogenically active and as such are effective in stimulating, accelerating, potentiating or otherwise enhancing the wound healing process can be usefully applied to the suture herein, e.g., hEGF (urogastrone), TGF-beta, IGF, PDGD, FGF, etc. These and other useful HGFs and closely related HGF derivatives, methods by which they can be obtained and methods and compositions featuring the use of HGFs to enhance wound healing are variously disclosed, inter alia, in U.S. Pat. Nos. 3,883,497, 3,917,824, 3,948,875, 4,338,397, 4,418,691, 4,528,186, 4,621,052, 4,743,679, 4,717,717, 4,861,757, 4,874,746 and 4,944,948. European Patent Application Nos. 46,039, 128,733, 131,868, 136,490, 147,178, 150,572, 177,915 and 267,015, PCT International Applications WO 83/04030, WO 85/003698, WO 85/01284 and WO 86/02271 and UK Patent Applications GB 2 092 155 A, 2 162 851 A and GB 2 172 890 A, and, "Growth Factors in Wound Healing", Lynch et al, J. Clin. Invest., Vol. 84, pages 640–645 (August 1989), all of which are incorporated by reference herein. Of the known HGFs, hEGF, TFG-beta, IGF, PDGF and FGF are preferred, either singly or combination.

In a preferred embodiment of a braided suture, a filling composition comprising a surgical wound healing enhancing amount of at least one HGF and as carrier therefor at least one water soluble, liquid polyhydroxy compound and/or ester thereof is applied to the suture. The carrier protects the HGF component of the filling composition from excessive degradation or loss of biopotency during storage and as disclosed above, when the suture is fabricated from an absorbable resin which is susceptible to hydrolysis, the carrier improves the storage stability of the suture as well. In addition to the carrier, the HGF can contain a thickener such as any of those previously mentioned in order to reduce the tendency of carrier run-off.

The filling composition can contain one or more additional components which promote or enhance the wound healing effectiveness of the HGF component. Thus, e.g., site-specific hybrid proteins can be incorporated in the filling composition to maximize the availability of the HGF at the wound site and/or to potentiate wound healing. See e.g., Tomlinson (Ciba-Geigy Pharmaceuticals, West Sussex, U.LK.), "Selective Delivery and Targeting of Therapeutic Proteins", a paper presented at a symposium held Jun. 12-14, 1989 in Boston, Mass., the contents of which are incorporated by reference herein. The HGFs can also be associated with carrier proteins (CPs), e.g., in the form of CP-bound HGF(s), to further enhance availability of the HGF(s) at a wound site as disclosed in "Carrier Protein-Based Delivery of Protein Pharmaceuticals", a paper of Bio-Growth, Inc., Richmond, Calif. presented at the aforementioned symposium, the contents of said paper being incorporated by reference herein. The HGFs can also be incorporated in liposomes to provide for their release over an extended period. Lactate ion can be present to augment the wound healing activity of the HGF. Protectants for the HGF can also be utilized, e.g., polyoxyethylene glycols, acetoxyphenoxy polyethoxy ethanols, polyoxyethylene sorbitans, dextrans, albumin, poly-D-alanyl peptides and N-(2-hydroxypropyl)methacrylamide (HPMA).

The amounts of HGF, carrier and optional component(s) such as thickener, site-specific hybrid protein, carrier protein, etc., identified above can vary widely and in general will be at least that amount of a particular component which is required to perform its respective function in an effective way. Those skilled in the art employing known or conventional procedures can readily determine optimum amounts of each component for a particular filling composition and particular braided suture filled therewith.

In general, the HGF(s) can be present in the total composition at a level ranging from about 0.1 to about 25,000 micrograms per gram of such composition, preferably from about 0.5 to about 10000 micrograms per gram of composition and most preferably from about 1 to about 5000 micrograms per gram of composition.

Application of the HGF-containing composition to the braided suture of this invention can be carried out by any suitable technique, e.g., by any of the procedures described above for applying a storage stabilizing agent to the suture.

Suture Coating

It is also advantageous to apply one or more coating compositions to a braided suture component where particular functional properties are desired. For example, the suture can be coated with a material which improves its surface lubricity and/or knot tie-down characteristics. Coating materials for sutures are known and include non-bioabsorbable substances such as silicone, beeswax, or polytetrafluoroethylene, as well as absorbable substances such as homopolymers and/or copolymers of glycolide and lactide, polyalkylene glycols, and higher fatty acids or salts or esters thereof. Other suitable materials which impart either or both characteristics have been proposed in U.S. Pat. Nos. 3,867,190; 3,942,532; 4,047,533; 4,452,973; 4,624,256; 4,649,920; 4,716,203; and 4,826,945. Preferred bioabsorbable coating compositions can be obtained by copolymerizing in accordance with known procedures (1) a polyether glycol selected form the group consisting of relatively low molecular weight polyalkylene glycol, e.g., one corresponding to the general formula $HO(RO)_yH$ wherein R is an alkylene group of from 2–4 carbon atoms and y is an integer of from about 100–350, and polyethylene oxide-polypropylene oxide block copolymer, e.g., one corresponding to the general formula $H(OCH_2CH_2)_x(OC_3H_6)_y(OCH_2CH_2)_zOH$ wherein x is an integer of from about 45–90, y is an integer of from about 60–85 and z is an integer of from about 45–90 with (2) a mixture of lactide monomer and glycolide monomer or a preformed copolymer of lactide and glycolide, the weight ratio of (1) to (2) preferably ranging from about 4:1 to about 1:4 and more preferably from about 2:1 to about 1:2. The ratio of lactide to glycolide in the monomer mixture or in the copolymer of these monomers preferably varies from about 65–90 mole percent lactide and 10–35 mole percent glycolide. Polyether glycols which can be used to prepare the bioabsorbable coating composition advantageously include polyethylene glycols having molecular weights of about 3,500–25,000 and preferably from about 4,000–10,000 and polyethylene oxide-polypropylene oxide block copolymers having molecular weights of from about 5,000–10,000 and preferably from about 7,500 to about 9,000, e.g., those disclosed in U.S. Pat. Nos. 2,674,619, 3,036,118, 4,043,344 and 4,047,533 and commercially available as the Pluronics (BASF-Wyandotte). Where preformed copolymers of lactide and glycolide are employed in preparing the bioabsorbable coating compositions, they may be prepared as described in U.S. Pat. No. 4,523,591. The amounts of bioabsorbable coating composition to be applied to the suture, e.g., by coating, dipping, spraying or other appropriate techniques, will vary depending upon the specific construction of the suture, the size and the material of this construction. In general, the coating composition applied to an unfilled suture will constitute from about 1.0 to about 3.0 percent by weight of the coated suture, but the amount of coating add on may range from as little as about 0.5 percent, by weight, to as much as 4.0 percent or higher. For a preferred filled (i.e. containing a storage stabilizing agent) braided suture, amounts of coating composition will generally vary from about 0.5% to 2.0% with as little as 0.2% to as much as 3.0%. As a practical matter and for reasons of economy and general performance, it is generally preferred to apply the minimum amount of coating composition consistent with good surface lubricity and/or knot tie-down characteristics and this level of coating add on is readily determined experimentally for any particular suture.

Suture Calendering

In accordance with the invention, it has been found to be desirable to calender the braided suture prior to coating and/or filling in order to facilitate penetration of the coating or filler into the interstices of the braid suture.

Referring to FIG. 1, a braided suture 1 is moved axially in the direction indicated by arrow A. The suture is first passed between two cylindrical calendering rollers 2 and 3, each of which has a smooth, polished surface. The rollers are rotatably mounted in a calendering apparatus (not shown) such that one of the rollers is fixed with respect to translational movement whereas the other of the two rollers is biased, for example by a spring means, towards the fixed roller. The biasing force may be set to any desired predetermined magnitude. Alternatively, both rollers may be biased towards each other.

The rollers 2 and 3 are parallel to each other, but transverse to the axial orientation of suture 1. They apply a mechanical compression force to the suture in a direction as shown by arrows B.

When the suture 1 passes between rollers 2 and 3, it is compressed radially inward in direction B, but it expands laterally in the transverse direction, which opens up the braid structure. After passing between the first pair of rollers 2 and 3, suture 1, without turning or twisting, then preferably passes between a second pair of calendering rollers 4 and 5 which operate in the same manner as rollers 2 and 3, except that the second pair of rollers are oriented transversely to the first pair of rollers 2 and 3, as well as transversely to the suture 1. Thus, rollers 4 and 5 compress the suture laterally in a direction C which is transverse to direction B. The suture braids are then opened in a direction transverse to C and the suture is caused to return to its original, substantially round configuration. Preferably, the upper and lower roller pairs are positioned so that the suture rests against the surface of the fixed roller and is contacted and compressed by the action of the spring-loaded roller pressing against the suture and fixed roller.

Having passed between both pairs of rollers, the braids are uniformly opened to a predetermined extent, which facilitates application of filler material and/or coating material.

Figure 2:
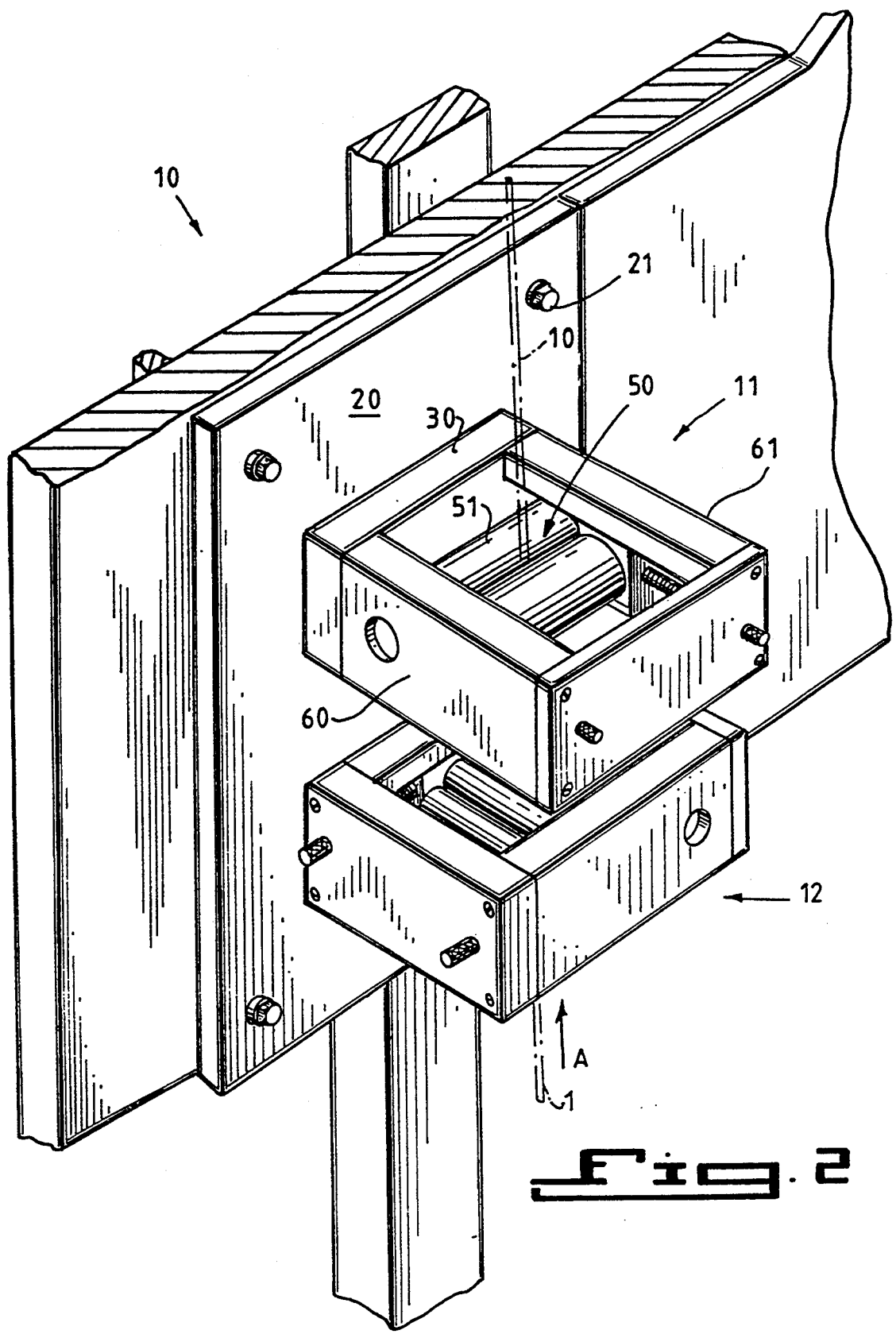
FIG. 2 is a perspective view of the calendering apparatus of the present invention.

FIGS. 2 and 3 respectively illustrate a perspective view of the calendering apparatus and an exploded perspective view of the upper portion 11 of the apparatus 10 for calendering sutures. FIG. 4 is a partially cut away detailed view of the spring mounting of the apparatus of the present invention.

Referring to FIG. 2, adapter plate 20 provides a means for mounting the apparatus to any appropriate receiving surface. Bolts 21 disposed through apertures in the adapter plate 20 secure the adapter plate 20 to the receiving surface.

Upper calender fixture 11 includes a backplate 30, and a fixed roller 50 rotatably mounted between left and right guides 60 and 61 respectively. The fixed roller 50 has a platen 51 with a surface of sufficient smoothness not to damage the suture. Bearing ends 52 fit into countersunk holes 62 in the left and right guides. Slide plates 80 and 81 are slidably mounted within respective slots 63 and 64 in the left and right guides. Floating roller 55 is rotatably mounted between slide plates 80 and 81 and is parallel to roller 50. Platen 56 of roller 55 has a surface of sufficient smoothness so as not to damage a suture being calendered. Surface smoothness for the calendering rollers of the present invention is preferably a fine surface finish in the range of about 4 to 16 microinches, and most preferably about 8 microinches, (i.e. the root mean square difference between the surface peaks and valleys) and can be achieved by electropolishing, lapping, or superfinishing.

Since slide plates 80 and 81 are movable within slots 63 and 64, floating roller 55 is movable toward and away from fixed roller 50. Compression springs 90 urge the floating roller 55 toward the fixed roller 50 by applying a biasing force of predetermined magnitude. Springs 90 are disposed around retainer rods 70 between front support plate 40 and respective slide plates 80 and 81. Retainer rods 70 are disposed through apertures 41 in the front support plate 40. Threaded ends 72 of the retainer rods are received into tapped holes 83 and 84 of the slide plates 80 and 81. The spring size and type is chosen so as to apply an appropriate biasing force. The biasing force must be sufficient magnitude to compress the suture, but less than that which would cause permanent damage to the suture.

In an attempt to qualify the amount of suture compression during calendering, sutures of different sizes were passed through one set of calender rolls, e.g. the upper portion 11 of the calendering device. The average diameter of the suture prior to application of the calender rolls and the average diameter in the narrowest direction, i.e. the direction of compression, were determined using an optical microscope. The percentage of compression of the suture is determined from the following formula:

$$\frac{D_1 - D_2}{D_1} \times 100$$

wherein:
$D_1$ = average suture diameter before calendering
$D_2$ = average suture diameter after calendering (in one direction only) as measured across the narrowest direction, i.e. the direction in which the compression force is applied.

An acceptable range of suture compression is from about 0 to 20%. A preferred range of suture compression is about 0 to 10%. Most preferred is a suture compression of about 5%.

A helical compression spring 90 should be chosen so as to apply biasing force to achieve suture compression within the above mentioned ranges. As stated, springs 90 are disposed around rods 70 between the inside surface of plate 40 and slide plates 80 and 81. In a preferred configuration with rollers 50 and 55 touching, the space between plate 40 and slide plates 80 and 81 is slightly less than about 2 inches, such as about 1¾ inches. In this configuration, a spring which has been found to be suitable has a free length of about 2″ and a spring rate of 2.0 lbs./in.

The bottom portion of the fixture 12 is similar to the top portion 11 except that it is mounted to the adapter plate 20 in an orientation orthogonal to that of top portion 11. It has been found that most sutures can be calendered at relatively high velocity, on the order of about 50 meters per minute, which is conducive to calendering in line immediately before the coating or filling operation, as explained in more detail below. However, smaller size sutures, e.g. sizes 6/0, 7/0 and 8/0, may require calendering at a slower speed, on the order of about 25 meters per minute, to provide more gentle suture handling and avoid filament breakage.

Filling

Figure 6:
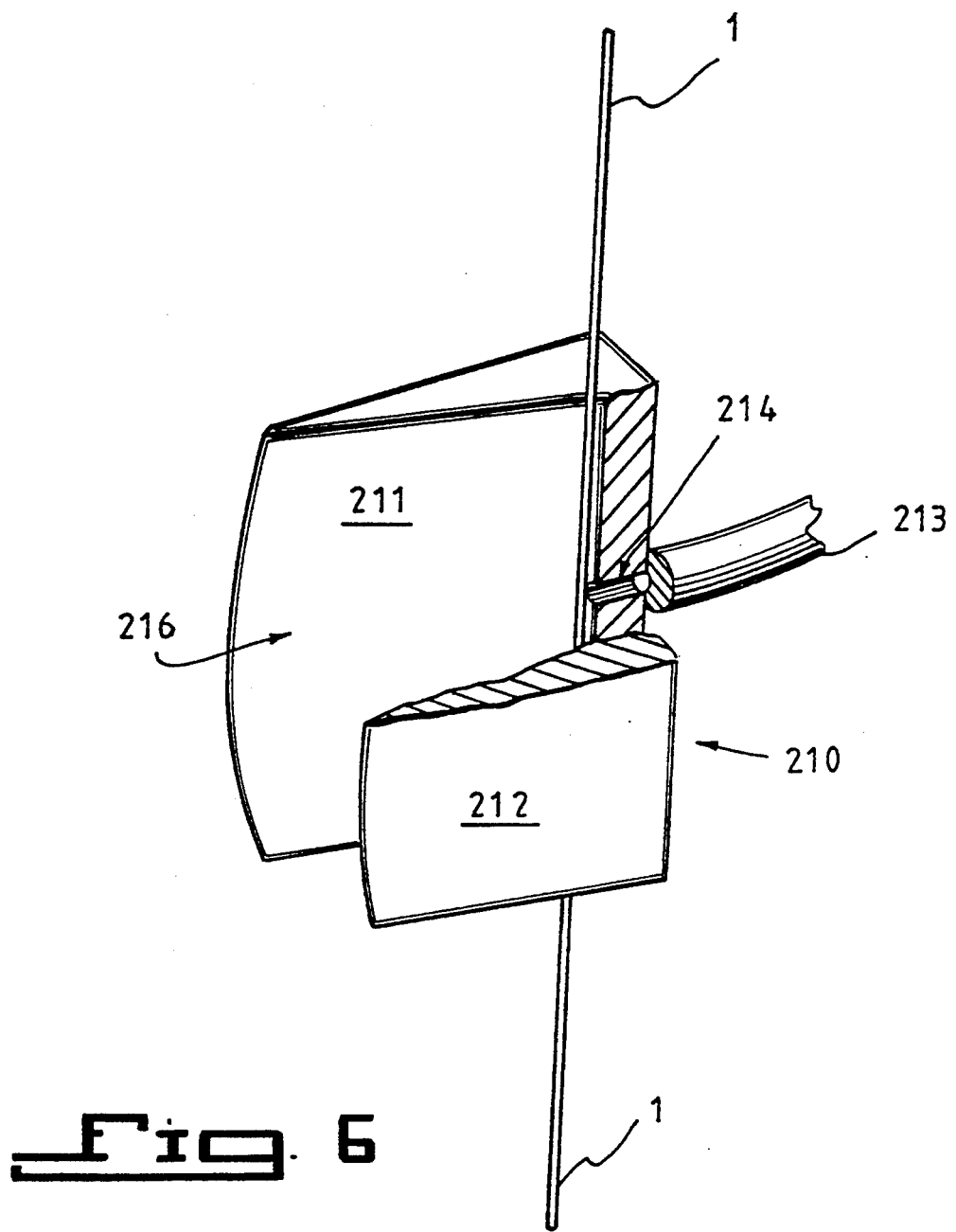
FIG. 6 is a partially cutaway perspective view of the filling head.

After the suture has been calendered it may be filled with appropriate filling agents as described above by passing the suture through a filling head. Filling heads are applicators for applying a fluid medium to the running length of an indefinite length work, such as a fiber or thread. Such an apparatus is available from Bouligny Company of Charlotte, N.C., and may include the applicator head designated as part number 503-488 of the Bouligny Company. An example of such a filling head is illustrated in FIG. 6. Filling solution may be continuously delivered from a reservoir by means of a standard metering pump.

In contrast to batch processes wherein the entire length of a suture is immersed in a trough of filling solution, use of the filling method of the present invention possesses the advantage of efficient use of filling solution. Only a small quantity of filling solution need be prepared at any one time. Thus, the method of the present invention enables the use of HGFs or other therapeutic agents such as those discussed above, which may be prohibitively expensive to formulate in solution in large quantity.

Figure 5:
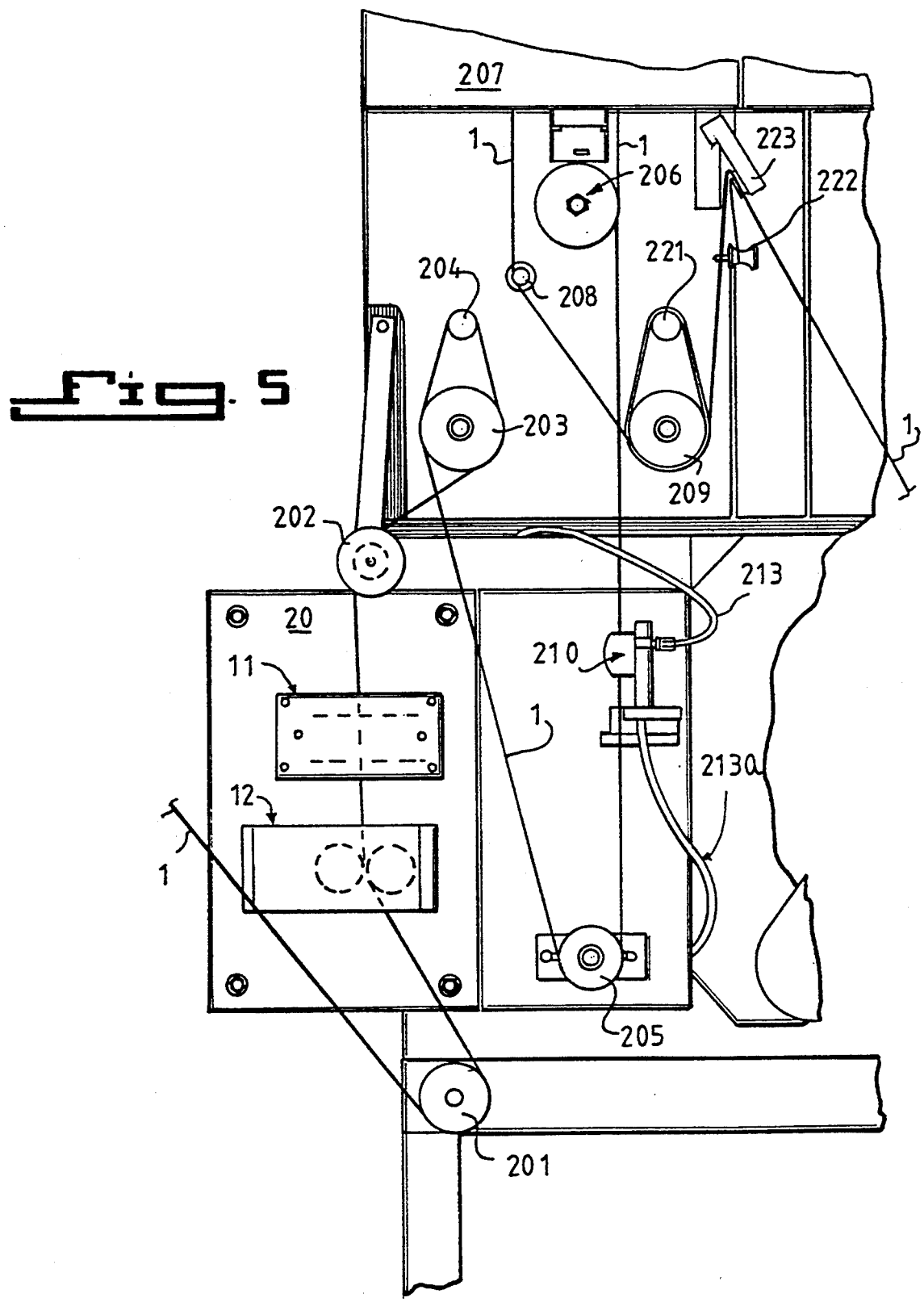
FIG. 5 is an elevational view of the suture filling apparatus of the present invention.

FIG. 5 illustrates the preferred apparatus for filling the suture in conjunction with the calendering apparatus. Suture 1 is drawn off a winding roll (not shown) and passes around roller 201 and up through calendering portions 12 and 11. The suture 1 is then guided around rollers 202, 203, 204 and 205, and passed vertically through filling head 210.

Referring now to FIG. 6, filling head 210 includes two wing portions 211 and 212 which define a V-shaped notch 216 through which the suture 1 is passed. A filler supply tube 213 provides means for carrying filling solution from a metering pump to the filling head 210. The filling solution passes through aperture 214 so as to enter the V-shaped notch region 216 along the corner edge defined by the intersection of the inner surfaces of wing portions 211 and 212. The filling solution accumulates to some extent along the interior walls of the V-shaped notch 216. As suture 10 passes through V-shaped notch 216 it is wetted and filled by the filling solution, which is substantially continuously applied by means of the metering pump. The term "substantially continuously" also includes the intermittent application of filling solution to maintain a predetermined minimum accumulation of filling agent in the filling head as the suture continuously passes therethrough. The filling head 210 can be fabricated from any material suitable for the purpose described herein, such as metal or plastic.

Referring again to FIG. 5, excess filling solution is collected and returned through a return conduit 213a to the filling solution reservoir, further conserving filling solution. After the suture is passed through the filling head 210 it is passed into a vertical oven 207 wherein it is heated so as to dry the suture. The oven is preferably maintained at a temperature of about 84 degrees Centigrade. The suture passes to the top of the oven without contacting any surface until it passes around a driver roller at the top of the oven. The filler dries rapidly in the heated oven, so that the suture substantially dries in the time required for the suture to travel to the top of the oven. Optionally, the suture may be guided around roller 206 and up again into oven 207 for as many multiple passes through the oven 207 as is desired. After calendering tension may be applied to the suture so as to produce up to about a 5% stretch in the suture. The suture speed is held constant throughout the procedure. After the final pass through the oven 207, suture 1 is guided around rollers 208, 209, 221, 222, 223 and onto a winding spool (not shown) or other suitable receiver.

The filling operation is controlled to consistently apply a uniform amount of filler to a given size suture. For each suture size a particular filling solution is used and a target filling amount, expressed as percent weight of the final suture, is selected. The pump capacity, braid velocity, suture denier, filling solution concentration, and target fill value are used to determine the appropriate pump speed to achieve the desired filling of the suture.

In accordance with the invention, the metering pump rate in rotations per minute, RPM, is calculated for any given suture using equations (1) to (5):

$$RPM = (REQD/CNC)/CAP \quad (1)$$

$$REQD = BRD \times TARG./(100 - TARG) \quad (2)$$

$$BRD = GMET \times VEL \text{ (meters per min.)} \quad (3)$$

$$GMET \text{ (grams per meter)} = DEN/9,000 \quad (4)$$

$$CNC \text{ (gm/ml.)} = \frac{\text{grams glycerol in solution}}{\text{milliliters of solution}} \quad (5)$$

wherein:
 BRD = suture mass velocity in grams per minute
 TARG = target fill rate in percentage of suture weight
 GMET = suture linear density in grams per meter
 VEL = suture velocity in meters per minute
 DEN = suture denier
 CNC = glycerol concentration in grams per ml. or grams per cc.
 CAP = pump capacity in cc. per revolution.

One appropriate concentration is about 370 grams of glycerol per 933 milliliters of solution, so for this case CNC = 0.3966. For suture sizes 6/0, 7/0 and 8/0 the preferred filling solution has a ratio of glycerol to calcium lactate of about 10:1 is used, and for all other suture sizes the ratio preferably is about 6.5:1. Preferred values for the remaining parameters (other than denier) needed to determine the pump rate are set forth in Table 1. Variable pump capacity may be achieved with a single metering pump by providing a variable setting flow valve with recirculating loops. Thus, at less than maximum pump capacity at least some filling solution is returned to the reservoir instead of to the applicator head.

TABLE 1

| Suture Size | VEL (Meters per Min.) | TARG (% suture weight) | CAP (cc per rev.) |
|---|---|---|---|
| 8/0 | 50 | 15 | .02 |
| 7/0 | 50 | 15 | .02 |
| 6/0 | 50 | 15 | .02 |
| 5/0 | 50 | 13 | .08 |
| 4/0 | 50 | 12 | .08 |
| 3/0 | 50 | 12 | .08 |
| 2/0 | 50 | 12 | .08 |
| 0 | 50 | 12 | .08 |

TABLE 1-continued

| Suture Size | VEL (Meters per Min.) | TARG (% suture weight) | CAP (cc per rev.) |
|---|---|---|---|
| 1 | 50 | 12 | .08 |
| 2 | 50 | 12 | .08 |
| 3 | 50 | 12 | .08 |

Denier of the suture material to be filled is measured and a metering pump rate is calculated for the suture material using equation (1) and the values set forth above.

In order to facilitate implementation of the filling operation in production, a computer program has been developed and may be used to reduce operator error. A flow chart of the program is shown in FIG. 7, the steps of which are described below.

Figure 7:
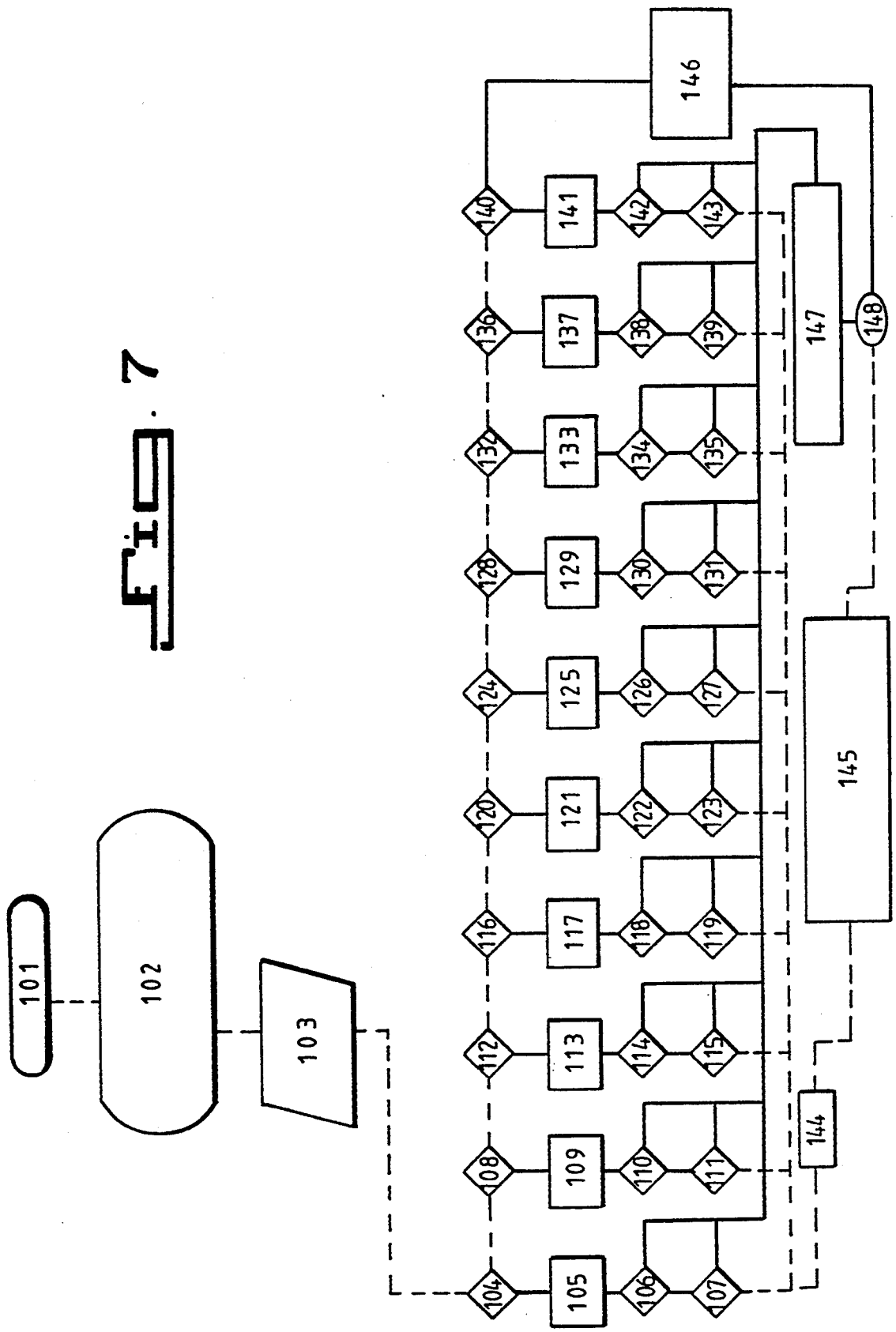
FIG. 7 is a flowchart of a computer program for controlling the filling method of the present invention.

The user initiates the program and the computer proceeds according to the following steps as shown in FIG. 7.

Step 101—Start of program

Step 102—The computer asks the user the following questions:
 1) What is the size of the braid?
 2) What is the braid lot number?
 3) What is the denier of the braid?

Step 103—The user inputs size, lot number, and denier of the suture to be filled.

Step 104—The computer then determines whether the suture size specified by the user was 8/0. If no, the program proceeds Step 108. If yes, the program proceeds to Step 105.

Step 105—The computer selects a pump capacity flow valve setting of 0.02 cc per revolution, a suture velocity of 50 meters per minute; a target add on percentage of 15% fill; and a drying oven temperature of 84° C.

Step 106—The computer determines whether the denier input by the user in Step 103 was less than 33. If yes, then the program goes to Step 147 and the user is told that the denier does not match the braid size, and that another denier sample should be taken before continuing. If no, then the program proceeds to Step 107.

Step 107—The computer determines whether the denier input by the user in Step 103 was greater than 50. If yes, the program moves to Step 147. If no, the program proceeds to Step 144 wherein pump rotations per minute (RPM) is calculated using equation (1) and the procedure advances to step 145.

Step 108—The computer determines whether the size of braid input by the user in Step 103 was 7/0. If no, the program moves to Step 112. If yes, the program advances to Step 109.

Step 109—The computer selects the following settings:
 Pump capacity = 0.02 cc/rev.
 Suture velocity 50 meters/min.
 Target add on = 15% fill
 Drying oven temp. = 84° C.

Step 110—The computer determines whether the denier size input by the user in Step 103 is less than 40. If yes, the program proceeds to Step 147. If no, the program advances to Step 111.

Step 111—The computer determines whether the denier size input by the user is above 60. If yes, the program goes to Step 147. If no, the program advances to Step 144.

Step 112—The computer determines whether the size of the braid input by the user in Step 103 was 6/0. If no, the program goes to Step 116. If yes, the program advances to Step 113.

Step 113—The computer selects the following settings:
Pump capacity=0.02 cc/rev.
Suture velocity=50 meters/min.
Target add on 15% fill
Drying oven temp.=84° C.

Step 114—The computer determines whether the denier input by the user in Step 103 is less than 50. If yes, the program goes to Step 147. If no, the program proceeds to Step 115.

Step 115—The computer determines whether the denier input by the user is above 160. If yes, the program goes to Step 147. If no, the program proceeds to Step 144.

Step 116—The computer determines whether the size of the braid input by the user in Step 103 was 5/0. If no, the program goes to Step 120. If yes, the program advances to Step 117.

Step 117—The computer selects the following settings:
Pump capacity=0.08 cc/rev.
Suture velocity=50 meters/min.
Target add on=13% fill
Drying oven temp.=84° C.

Step 118—The computer determines whether the denier input by the user in Step 103 is less than 250. If yes, the program goes to Step 147. If not, the program proceeds to Step 119.

Step 119—The computer determines whether the denier input by the user is above 340. If yes, the program moves to Step 147. If no, the computer proceeds to Step 144.

Step 120—The computer determines whether the size of the braid input by the user in Step 103 was 4/0. If no, the program goes to Step 124. If yes, the program advances to Step 121.

Step 121—The computer selects the following settings:
Pump capacity=0.08 cc/rev.
Suture velocity=50 meters/min.
Target add on 12% fill
Drying oven temp.=84° C.

Step 122—The computer determines whether the denier input by the user in Step 103 is less than 350. If yes, the program goes to Step 147. If no, the program advances to Step 123.

Step 123—The computer determines whether the denier input by the user is above 500. If yes, the program goes to Step 147. If no, the program advances to Step 144.

Step 124—The computer determines whether the size of the braid input by the user in Step 103 was 3/0. If no, the program moves to Step 128. If yes, the program advances to Step 125.

Step 125—The computer selects the following settings:
Pump capacity=0.08 cc/rev.
Suture velocity=50 meters/min.
Target add on=12% fill
Drying oven temp.=84° C.

Step 126—The computer determines whether the denier input by the user in Step 103 is less than 500. If yes, the program moves to Step 147. If no, the program advances to Step 127.

Step 127—The computer determines whether the denier input by the user in Step 103 is above 900. If yes, the program moves to Step 147. If no, the program proceeds to Step 144.

Step 128—The computer determines whether the size of the braid input by the user in Step 103 was 2/0. If no, the program goes to Step 132. If yes, the program goes to Step 129.

Step 129—The computer selects the following settings:
Pump capacity 0.08 cc/rev.
Suture velocity 50 meters/min.
Target add on 12% fill
Drying oven temp.=84° C.

Step 130—The computer determines whether the denier input by the user in Step 103 is less than 1,000. If yes, the program moves to Step 147. If no, the program goes to Step 131.

Step 131—The computer determines whether the denier input by the user in Step 103 is above 1,350. If yes, the program moves to Step 147. If no, the program advances to Step 144.

Step 132—The computer determines whether the size of the braid input by the user in Step 103 was size 0. If no, the program goes to Step 136. If yes, the program proceeds to Step 133.

Step 133—The computer selects the following settings:
Pump capacity 0.08 cc/rev.
Suture velocity 50 meters/min.
Target add on 12% fill
Drying oven temp.=84° C.

Step 134—The computer determines whether the denier input by the user in Step 103 is less than 1,400. If yes, the program moves to Step 147. If no, the program advances to Step 135.

Step 135—The computer determines whether the denier input by the user is above 1,950. If yes, the program goes to Step 147. If no, the program goes to Step 144.

Step 136—The computer determines whether the size of the braid input by the user in Step 103 was size 1. If no, the program advances to Step 140. If yes, the program proceeds to Step 137.

Step 137—The computer selects the following settings:
Pump capacity=0.08 cc/rev.
Suture velocity=50 meters/min.
Target add on=12% fill
Drying oven temp.=84° C.

Step 138—The computer determines whether the denier input by the user in Step 103 is less than 2,000. If yes, the program goes to Step 147. If no, the program goes to Step 139.

Step 139—The computer determines whether the denier input by the user is above 2,600. If yes, the program goes to Step 147. If no, the program goes to Step 144.

Step 140—The computer determines whether the size of the braid input by the user in Step 103 is size 2. If no, the program goes to Step 146. If yes, the program goes to Step 141.

Step 141—The computer selects the following settings:
Pump capacity=0.08 cc/rev.
Suture velocity=50 meters/min.
Target add on=12% fill
Drying oven temp.=84° C.

Step 142—The computer determines whether the denier input by the user in Step 103 is less than 3,000. If yes, the program does to Step 147. If no, the program goes to Step 143.

Step 143—The computer determines whether the denier input by the user in Step 103 is above 3,500. If yes, the program goes to Step 147. If no, the program goes to Step 144.

Step 144—The computer calculates the pump speed in rotations per minute in accordance with equation (1) and proceeds to step 145.

Step 145—The user is informed by printout or by monitor as to the lot number specified, the appropriate braid speed, pump rate, pump capacity setting, filling target percentage, and temperature of the drying chamber. The suture size, denier and filling solution identification are also displayed. The program thereafter runs to completion to Step 148.

Step 146—This step is arrived at if the suture size input by the user in Step 103 does not match any of the designated suture sizes pre-programmed in the computer. The user is informed that he has chosen an incorrect size designation. The program then moves to Step 148, which is the end.

Step 147—The user is warned that the denier which he has input in size 103 does not match the size of braid which he has also input in 103. The user is advised to take another denier sample before continuing. The program then moves to Step 148.

Step 148—End of program.

The program may be expanded to accommodate different size sutures, and the processing conditions for any particular suture may readily be modified without affecting the conditions for other size sutures. Although the program has been described in the context of printing out processing conditions in terms of settings to be adjusted by the user, it is contemplated that one or more processing conditions could be set automatically by computer control. Thus, the flow valve could be adjusted by electromechanical controls to the appropriate position, the godet or roller motor(s) could be automatically set to achieve the appropriate braid speed including, if desired, a stretch condition, the drying oven temperature could be set automatically and the metering pump could be electronically set to the appropriate RPM calculated from equation (1).

While many specifics have been described, it is contemplated that a wide range of processes could be developed which take advantage of the calendering and coating/filling operations described herein. Thus, the apparatus and computer program for filling may also be used to advantage to coat sutures with a lubricant coating in order to improve knot run down, irrespective whether the suture is absorbable or non-absorbable and is or is not to be filled. In this regard, numerous advantageous processes are contemplated.

By way of example, the apparatus, method and/or computer program described above for filling may be used to coat absorbable or non-absorbable sutures, and the sutures may be calendered prior to coating to improve coating efficiency. By way of further example, absorbable or non-absorbable sutures may be calendered and subsequently filled. Because the filling may contain desirable therapeutic agents and/or growth factors, filling may be desirable for both absorbable or non-absorbable sutures in order to administer such agents or growth factors. It has been found desirable to apply a lubricant coating, if any, prior to calendering and filling, but it is also contemplated that calendering and filling could precede the coating operation.

Numerous variations and modifications of the invention will occur to a person of ordinary skill in the art or will be learned by or from experimentation with the invention all within the scope of the appended claims.

What is claimed is:

1. An apparatus for calendering a multifilament suture, which comprises:
    a frame;
    a first pair of rollers including a first roller and a second roller, said first pair of rollers being rotatably mounted to said frame, said first and second rollers being substantially parallel to each other, and at least one of said first and second rollers being resiliently biased towards the other of said first and second rollers so as to apply a predetermined amount of compressive force to a suture located therebetween;
    a second pair of rollers including a third roller and a fourth roller, said second pair of rollers being rotatably mounted to said frame, said third and fourth rollers being substantially parallel to each other and substantially orthogonal to said first pair of rollers, at least one of said third and fourth rollers being resiliently biased towards the other of said third and fourth rollers so as to apply a predetermined amount of compressive force to a suture located therebetween;
    wherein each of said first, second, third and fourth rollers is substantially cylindrical and has a polished suture-contacting surface with a surface smoothness of from about 4 microinches to about 16 microinches.

2. The apparatus of claim 1 wherein each said compressive force is sufficient to achieve a suture compression of from about 0% to about 20%, wherein said suture compression is defined as the ratio of average suture diameter before said suture is passed between one of said first or second pair of rollers and the average suture diameter in the narrowest direction after said suture is passed between said one of said first or second pair of rollers, said suture diameter being measured in substantially the same linear direction in which the compressive force is applied to the suture.

3. The apparatus of claim 1 wherein one roller of each of said first and second pairs is laterally fixed, and the other roller of each of said first and second pairs is laterally movable and biased towards the laterally fixed roller.

4. The apparatus of claim 3 wherein each of said laterally movable rollers is mounted at its end to side plates, said side plates being slidably disposed in slots in said frame.

* * * * *